US008324171B1

(12) United States Patent
Burke et al.

(10) Patent No.: US 8,324,171 B1
(45) Date of Patent: *Dec. 4, 2012

(54) OPHTHALMIC COMPOSITIONS CONTAINING DIGLYCINE

(75) Inventors: Susan E. Burke, Batavia, NY (US); Erning Xia, Penfield, NY (US); Catherine A. Scheuer, West Henrietta, NY (US); Srini Venkatesh, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/366,399

(22) Filed: Feb. 6, 2012

(51) Int. Cl.
*A61K 38/00* (2006.01)
*A61K 31/14* (2006.01)

(52) U.S. Cl. .............. 514/19; 514/642; 514/912
(58) Field of Classification Search .............. 514/19, 514/642, 912
See application file for complete search history.

(56) References Cited

U.S. PATENT DOCUMENTS

| | | | |
|---|---|---|---|
| 4,409,205 A | 10/1983 | Shively | |
| 4,758,595 A | 7/1988 | Ogunbiyi et al. | |
| 4,820,352 A | 4/1989 | Riedhammer et al. | |
| 5,209,927 A | 5/1993 | Gressel et al. | |
| 5,244,799 A | 9/1993 | Anderson | |
| 5,294,607 A | 3/1994 | Glonek et al. | |
| 5,300,296 A | 4/1994 | Holly et al. | |
| 5,342,620 A | 8/1994 | Chowhan | |
| 5,494,937 A | 2/1996 | Asgharian et al. | |
| 5,505,953 A | 4/1996 | Chowhan | |
| 5,741,817 A | 4/1998 | Chowhan et al. | |
| 5,765,579 A | 6/1998 | Heiler et al. | |
| 5,800,807 A | 9/1998 | Hu et al. | |
| 6,143,799 A | 11/2000 | Chowhan et al. | |
| 6,331,523 B1 | 12/2001 | Kljavin et al. | |
| 6,365,636 B1 | 4/2002 | Chowhan et al. | |
| 6,429,220 B1 | 8/2002 | Yagi et al. | |
| 6,503,497 B2 | 1/2003 | Chowhan et al. | |
| 6,528,465 B1 | 3/2003 | Cantoro | |
| 6,620,797 B2 | 9/2003 | Chowhan et al. | |
| 6,806,243 B2 | 10/2004 | Hozumi et al. | |
| 6,995,123 B2 | 2/2006 | Ketelson et al. | |
| 7,578,996 B2 | 8/2009 | Yu et al. | |
| 2002/0010154 A1 | 1/2002 | Uchiyama et al. | |
| 2002/0142346 A1 | 10/2002 | Nestor, Jr. et al. | |
| 2003/0153622 A1 | 8/2003 | Hozumi et al. | |
| 2004/0071769 A1 | 4/2004 | Farnq et al. | |
| 2004/0132704 A1 | 7/2004 | Yanni et al. | |
| 2004/0137079 A1 | 7/2004 | Cooke | |
| 2004/0253280 A1 | 12/2004 | Chowhan et al. | |
| 2005/0074467 A1 | 4/2005 | Fujita et al. | |
| 2005/0137166 A1 | 6/2005 | Asgharian et al. | |
| 2005/0260280 A1 | 11/2005 | Cook et al. | |
| 2006/0122080 A1 | 6/2006 | Mori | |
| 2006/0127496 A1 | 6/2006 | Smith | |
| 2007/0149428 A1 | 6/2007 | Ammon et al. | |
| 2008/0095754 A1 | 4/2008 | Burke et al. | |

FOREIGN PATENT DOCUMENTS

| | | |
|---|---|---|
| EP | 0923950 A2 | 12/2000 |
| JP | 2005-068119 A1 | 3/2005 |
| JP | 2005-346099 A | 12/2005 |
| WO | WO 95/30414 A1 | 11/1995 |
| WO | WO 96/03484 A1 | 2/1996 |
| WO | WO 98/32421 A1 | 7/1998 |
| WO | WO 02/49615 A | 6/2002 |
| WO | WO 03/006046 A1 | 1/2003 |
| WO | WO 2006/055454 A2 | 5/2006 |
| WO | WO 2008/049043 A2 | 4/2008 |

OTHER PUBLICATIONS

Fujihara et al., "Lactoferrin suppresses loss of corneal epithelial integrity in a rabbit short-term dry eye model," J of Ocular Pharm, 1998, (vol. 14), (Issue. 2), (pp. 99-105).
Geerling et al., "Autologous serum eye drops for ocular surface disorders," Br J Ophthal, 2004, (vol. 88), (p. 1467-1474).
Intl Search Report and Opinion, "PCT/US2007/081715 filed Oct. 18, 2007," Bausch & Lomb Reference P04153.
Intl Search Report and Opinion, "PCT/US2007/081714 filed Oct. 18, 2007," Bausch & Lomb Reference P04571.
Intl Search Report and Opinion, "PCT/US2009/037600 filed Mar. 19, 2009," Bausch & Lomb Reference P04325.
MacLean et al., "Stabilization of proteins by low molecular weight multi-ions," J of Pharm Sci, Oct. 2002, (vol. 91), (Issue. 10), (p. 2220-2224).
Sitaramamma et al., "Effect of storage on protein concentration of tear samples," Current Eye Res, (p. 1027-1035), (Jul. 16, 1998).
Tetronic, "product information from the Chemicals Catalog," http://worldaccount.basf.com/wa/NAFTA-en_USCatalog/ChemicalsNAFTA/pi/BASF/Brand/tetronic?, (Dec. 3 ,2009).
Tsubota et al., "Treatment of dry eye by autologous serum application in Sjogren's syndrome," Br J Ophthal, 1999, (vol. 83), (p. 390-393).

*Primary Examiner* — Zohreh Fay
(74) *Attorney, Agent, or Firm* — Joseph Barrera

(57) ABSTRACT

Ophthalmic composition that includes 0.05% w/v to 2% w/v diglycine or a salt thereof; 1.0 ppm to 8.5 ppm alexidine, and 0.1% w/v to 2% w/v of one or more boron buffering compounds.

12 Claims, No Drawings

OPHTHALMIC COMPOSITIONS CONTAINING DIGLYCINE

This application claims the benefit of U.S. application Ser. No. 11/873,703 filed Oct. 17, 2007, now U.S. Pat. No. 8,138, 156, under 35 U.S.C. §120, which in turn claims the benefit of U.S. Provisional Application Ser. Nos. 60/852,488 and 60/852,539, both applications filed on Oct. 18, 2006, under 35 U.S.C. §119(e).

BACKGROUND OF THE INVENTION

The invention relates to ophthalmic compositions comprising diglycine and a boron buffering compound. The ophthalmic compositions are useful as eye drops, e.g., as in a rewet drop or a pharmaceutical formulation, or as a lens care solution for disinfecting, cleaning or packaging contact lenses.

Various antimicrobial agents are known for use as preservatives in ophthalmic compositions. The antimicrobial agents should have a broad spectrum of antimicrobial activity but must also be non-irritating to the eye. Some of the most common antimicrobial agents used in ophthalmic applications include benzalkonium chloride, chlorhexidine, polyquaternium-1, poly(hexamethylene biguanide), alexidine, and thimerosal.

Each antimicrobial compound has its own degree of efficacy against a specific collection of microorganisms. Because a single antimicrobial agent may not necessary be efficacious against all microorganisms of interest in a safe and effective concentration range, it is sometimes beneficial to introduce another compound into the formulation to enhance disinfection or preservative efficacy against the microorganisms. Some compounds, if added, provide an improvement in antimicrobial activity of another agent or alone have mild antimicrobial properties. U.S. Pat. No. 5,817,277 describes the use of tromethamine in combination with several antimicrobial agents or as an antimicrobial agent to disinfect contact lenses. U.S. Pat. Nos. 5,342,620; 5,505,953; and 6,503,497 describe that a complex of borate buffer and one or more polyols can improve the antimicrobial efficacy of an ophthalmic solution.

U.S. Pat. Nos. 6,319,464 and 6,949,218 describe that low molecular weight amino alcohols such as 2-amino-2-methyl-1-propanol (AMP), 2-dimethylamino-2-methyl-1-propanediol (DMAMP), 2-amino-2-ethyl-1,3-propanediol (AEPD), 2-amino-2-methyl-1,3-propanediol (AMPD), and 2-amino-1-butanol (AB) can enhance the activity of antimicrobial agents such as various biguanides including chlorhexidine, alexidine and poly(hexamethylene biguanide) (PHMB). PCT Publ. No. WO95/30414 discloses the use of one or more amino acids in a specified range increased the antimicrobial activity, particularly against Acanthamoeba. Compositions are disclosed that include glycine and histidine. US Publ. Nos. US20030153622 and US20060122080 disclose the optional use of neutral amino acids, including glycine, in combination with an amino alcohol, an acid including glycolic acid and aspartic acid.

European Patent No. 0923950 discloses the combination of polyquaternium-1, an amino acid and a non-ionic tonicity adjusting agent. A specific example of histidine in combination with a phosphate buffer was disclosed. U.S. Pat. No. 5,494,937 discloses the combination of a borate buffer, an amino acid (e.g., alanine, glycine and histidine) and a polyol.

There continues to be a need for ophthalmic compositions with improved disinfecting systems that are simple to use, are effective against a broad spectrum of microorganisms, are non-toxic and do not cause ocular irritation. There is also a need for ophthalmic compositions that maintain some buffering capacity such as contact lens packaging solutions and preservative-free solutions.

SUMMARY OF THE INVENTION

Ophthalmic composition that includes 0.05% w/v to 2% w/v diglycine or a salt thereof; 1.0 ppm to 8.5 ppm alexidine, and 0.1% w/v to 2% w/v of one or more boron buffering compounds. The ophthalmic compositions can be used to disinfect contact lenses upon soaking the lenses in the composition for a minimum of one to four hours.

DETAILED DESCRIPTION OF THE INVENTION

Diglycine in combination with one or more boron buffering compounds is used to enhance the biocidal efficacy against most of the microorganisms tested for ophthalmic applications. The term "boron buffering compound" refers to a boron compound that provides buffering capacity to the composition.

Borate buffering systems are well characterized buffer systems and are presently used in ophthalmic compositions, particularly in contact lens care solutions. For example, U.S. Pat. No. 4,758,595 to Ogunbiyi et al. describes that a contact-lens solution containing a polyaminopropyl biguanide (PAPB), also known as PHMB, can exhibit enhanced efficacy if combined with a borate buffer. Borate buffering compounds include, for example, boric acid and borate salts, e.g., sodium borate or potassium borate, and potassium tetraborate or potassium metaborate that produce boric acid or its salt in solutions. Generally, the boron buffering compounds are present from 0.05% to 2.5% (w/v) or from 0.1% to 10.5% (w/v).

In addition, the ophthalmic compositions include diglycine, which is present in the composition at a concentration of from 0.05% w/v to 2% w/w or 0.1% w/v to w/v.

In one embodiment, the one or more boron buffering compounds include boric acid from 0.15% w/v to 0.6% w/v, sodium or potassium borate from 0.05% w/v to 0.5% w/v. and the one or more polyglycines includes diglycine from 0.1% w/v to 0.7% w/v.

The term "ophthalmic composition" defines a composition intended for application in the eye or intended for treating a device to be placed in contact with the eye such as a contact lens. Ophthalmic compositions can include compositions for direct placement in the eye, including eye drop solutions such as for treating dry eye and rewetting contact lenses as well as for ophthalmic pharmaceutical formulations. Ophthalmic compositions also include those compositions formulated as multi-purpose solutions for cleaning and disinfecting contact lenses or to package contact lenses.

The ophthalmic composition can also include other buffer components that complement the one or more boron buffering compounds. For example, one or more phosphate components can be used with a boron buffering compound to achieve operational requirements, e.g., contact lens compatibility, of the composition. Exemplary phosphate components includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

One preferred buffer system is based upon a borate/phosphate buffer system. For example a combined boric/phosphate buffer system can be formulated from a mixture of boric acid/sodium borate and the monobasic/dibasic phosphates. In a combined boric/phosphate buffer system, the phosphate buffer is used (in total) at a concentration of 0.004 to 0.2 M (Molar), preferably 0.04 to 0.1 M. The borate buffer (in to is used at a concentration of 0.02 to 0.8 M, preferably 0.07 to 0.2 M.

The ophthalmic compositions can also include a cationic antimicrobial compound. Exemplary cationic antimicrobial compounds include, but are not limited to, quaternary ammonium salts used in ophthalmic applications such as α-[4-tris (2-hydroxyethyl)ammonium chloride-2-butenyl]poly[1-dimethylammonium chloride-2-butenyl]-ω-tris(2-hydroxyethyl) ammonium chloride (available as Polyquaternium-1® from Onyx Corporation), benzalkonium halides, and biguanides such as salts of alexidine, alexidine-free base, salts of chlorhexidine, hexamethylene biguanides and salts thereof and their polymers, antimicrobial polypeptides and mixtures thereof.

The term "cationic" when referring to an antimicrobial component refers to the predominant form of the antimicrobial component at neutral pH having a positive charge and a counteranion. An exemplary list of cationic disinfecting antimicrobial components include α-[4-tris(2-hydroxyethyl)ammonium chloride-2-butenyl]poly[1-dimethylammonium chloride-2-butenyl]-ω-tris(2-hydroxyethyl)ammonium chloride, poly(hexamethylenebiguanide) (PHMB), and any mixture thereof.

The cationic antimicrobial component is present in an amount from 0.01 ppm to 30 ppm, or from 0.1 ppm to 20 ppm. It is preferred, however, that the amount of antimicrobial compound used is effective in disinfecting contact lenses that are contacted with the compositions, while at the same time not causing patient discomfort.

In one embodiment, the primary antimicrobial component present in the lens care compositions is poly(hexamethylene biguanide), which is present from 0.1 ppm to 2 ppm. In another embodiment, the primary antimicrobial component present in the lens care compositions is α-[4-tris(2-hydroxyethyl)ammonium chloride-2-butenyl]poly[1-dimethylammonium chloride-2-butenyl]-ω-tris(2-hydroxyethyl) ammonium chloride, which is present from 1 ppm to 10 ppm.

Any one mixture of the two cationic antimicrobial components can also be present in the lens care compositions. For example, a particular lens care composition can include from 0.2 ppm to 1 ppm, preferably from 0.3 ppm to 0.8 ppm PHMB, and 1 ppm to 10 ppm α-[4-tris(2-hydroxyethyl)ammonium chloride-2-butenyl]poly[1-dimethylammonium chloride-2-butenyl]-ω-tris(2-hydroxyethyl) ammonium chloride.

In another embodiment, an oxidative antimicrobial compound can be used in the composition. Any oxidative antimicrobial compound known for use in contact lens solutions can be used such as hydrogen peroxide or a stabilized form of hydrogen peroxide, chlorine dioxide and chlorite ion precursor compounds.

The ophthalmic compositions can also include an amidoamine such as myristamidopropyl dimethylamine.

The ophthalmic compositions can also include any monoterpene, sesquiterpene and/or diterpene or derivatives thereof. Acyclic, monocyclic and/or bicyclic mono-, sesqui- and/or diterpenes, and those with higher numbers of rings, can be used. A "derivative" of a terpene as used herein shall be understood to mean a terpene hydrocarbon having one or more functional groups such as terpene alcohols, terpene ethers, terpene esters, terpene aldehydes, terpene ketones and the like and combinations thereof. Here, both the trans and also the cis isomers are suitable. The terpenes as well as the terpene moiety in the derivative can contain from 6 to about 100 carbon atoms and preferably from about 10 to about 25 carbon atoms.

Representative examples of suitable terpene alcohol compounds include verbenol, transpinocarveol, cis-2-pinanol, nopol, isoborneol, carbeol, piperitol, thymol, α-terpineol, terpinen-4-ol, menthol, 1,8-terpin, dihydro-terpineol, nerol, geraniol, linalool, citronellol, hydroxycitronellol, 3,7-dimethyl octanol, dihydro-myrcenol, tetrahydro-alloocimenol, perillalcohol, falcarindiol and the like and mixtures thereof.

The lens care solutions can also include one or more neutral or basic amino acids. The neutral amino acids include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1% to 5% (w/v).

The lens care solutions can also include glycolic acid, asparatic acid or any mixture of the two at a total concentration of from 0.001% to 4% (w/v) or from 0.01% to 2.0% (w/v).

The lens care solutions can also include glycolic acid, asparatic acid or any mixture of the two, in combination with 2-amino-2-methyl-1,3-propanediol or a salt thereof. In some cases, solutions that contain a mixture of two of the three, or all three, compounds minimize the change of the lens size following placement of the contact lens in the eye. The 2-amino-2-methyl-1,3-propanediol (AMPD) or the salt thereof is added to the solutions in an amount to satisfy a predetermined molar ratio of glycolic acid, asparatic acid or any mixture of the two and AMPD. The molar ratio of the two components glycolic acid and/or asparatic acid to AMPD is 1:20 to 1.3:1. The glycolic acid, asparatic acid or any mixture of the two is present in the compositions at a concentration of 0.01% to 5% (w/v) or at a concentration of 0.05% to 1% (w/v).

The amount of AMPD present in the solutions can be determined according to the amount of glycolic acid and/or asparatic acid in the composition. As stated, AMPD is present in an amount to provide a molar ratio of glycolic acid and/or asparatic acid to AMPD to be from 1:20 to 1.3:1, from 1:15 to 1.2:1 or from 1:14 to 1:1. If the amount of AMPD exceeds 20 mols per 1 mol of glycolic acid and/or asparatic, adsorption of the cationic antimicrobial component on the contact lens will occur. If the amount of AMPD is less than 1 mol per 1.3 mols of glycolic acid and/or asparatic acid, a reduction in antimicrobial efficacy of the composition is observed.

The lens care solutions will very likely comprise effective amounts of one or more known lens care formulation components such as a detergent or surfactant component, a viscosity inducing or thickening component, a chelating or sequestering component, or a tonicity component. The additional component or components can be selected from materials which are known to be useful in contact lens care solutions and are included in amounts effective to provide the desired effect or benefit.

Some of the common ophthalmic surfactants with known advantages in terms of cleaning efficacy and comfort are described in greater detail as follows. Suitable surfactants for use in the ophthalmic compositions need to be soluble in the ophthalmic compositions, need to be compatible with the other solution components, and need to be non-irritating to ocular tissue. The surfactants will generally be present in a total amount from 0.01% to 3% (w/v), from 0.1% to 2% (w/v), or from 0.1% to 1.5% (w/v).

Suitable surfactants include, but are not limited to polyethers based upon poly(ethylene oxide)-poly(propylene oxide)-poly(ethylene oxide), i.e., (PEO-PPO-PEO), or poly (propylene oxide)-poly(ethylene oxide)-poly(propylene oxide), i.e., (PPO-PEO-PPO), or a combination thereof.

PEO-PPO-PEO and PPO-PEO-PPO materials are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein by reference. The classes of nonionic polyalkoxylated copolymers known by the Poloxamer and Poloxamine tradenames can also be used.

Other suitable nonionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still other preferred surfactants include tyloxapol, betaine-type surfactants, polysulfates, polyethylene glycol, alkyl esters and any mixture thereof.

Some of the more preferred compositions will include an amphoteric surfactant. Suitable amphoteric surfactants include betaine and sulphobetaine surfactants. The betaine or sulphobetaine surfactants are believed to contribute to the disinfecting properties of the compositions by increasing the permeability of the bacterial cell wall, thus allowing an antimicrobial agent to enter the cell. Suitable betaine and sulphobetaine surfactants to be used in the compositions are the betaine/sulphobetaine-compounds that contain both basic and acidic groups which form an inner salt giving the molecule both cationic and anionic hydrophilic groups over a broad range of pH values. Some common examples of these compounds are described in U.S. Pat. Nos. 2,082,275, 2,702,279 and 2,255,082. Exemplary betaine and sulphobetaine surfactants are of the formula

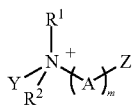

I wherein $R^1$ and $R^2$ are independently selected from a $C_1$-$C_4$ alkyl, e.g., methyl or ethyl;

A is an unsubstituted or a substituted alkylene with two to four carbons, and m is an integer from 2 to 4;

Y is a straight or branched alkyl, or a straight or branched alkene, with eight to sixteen carbons; and Z is $-SOC_3^-$ or $-CO_2^-$, preferably Z is $-SO_3^-$. In a particular embodiment, both $R^1$ and $R^2$ are methyl.

Examples of particularly suitable betaine surfactants include $C_2$ to $C_{18}$ alkyl dimethyl betaine such as coconutbetaine and $C_{10}$ to $C_{16}$, alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

One preferred sulphobetaine is N-decyl-N,N-dimethyl-3-ammonio-1-propanesulfonate available from Calbiochem Company as Zwittergent 3-10. See, also, U.S. Pat. No. 5,765,579.

As stated, the ophthalmic compositions also include one or more natural polymers selected from the group consisting of hyaluronic acid, condroitin sulfate, alginate, pectin and xanthan gum. The more preferred natural polymers are hyaluronic acid or salt thereof, and alginate. A mixture of hyaluronic acid and alginate can also be used. The concentration of the natural polymers in the compositions is from 0.05% w/v to 0.5% w/v or from 0.05% w/v to 0.2% w/v.

In one embodiment, the concentration of hyaluronic acid or salt thereof in the composition is from 0.05% w/v to 0.5% w/v or from 0.05% w/v to 0.2% w/v. The average molecular weight of the hyaluronic acid or salt thereof is from 500 kD to 5000 kD, or from 1000 kD to 3000 kD. In another embodiment, the concentration of alginate in the composition is from 0.05% w/v to 0.5% w/v or from 0.05% w/v to 0.2% w/v. In one embodiment, the average molecular weight of the alginate is from 50 kD to 3,000 kD or from 200 kD to 2000 kD.

Yet another suitable ophthalmic composition component comprises one or more viscosity control/wetting agents. Because of the demulcent effect of viscosity control and wetting agents, these materials have a tendency to enhance a contact lens wearer's comfort by providing a protective film thought to cushion the interaction between the eye surface and the lens. Suitable viscosity control/wetting agents include, for example, but are not limited to cellulose polymers like hydroxyethylcellulose, hydroxypropylcellulose or hydroxypropylmethylcellulose, polyquaternium-10, and carboxymethylcellulose; povidone; poly(vinyl alcohol), poly (ethylene oxide) and poly(N,N-dimethylacrylamide) and the like.

Viscosity control and wetting agents of the foregoing types are also described in greater detail in PCT Patent Application Nos. WO 04/093545 and WO 05/053759. Viscosity control/wetting agents are typically present in the ophthalmic compositions from 0.001 wt % to 1.0 wt %.

In one embodiment, a mixture of hyaluronic acid or salt thereof, or alginate, and hydroxypropylmethylcellulose is present in the composition. The concentration of hydroxypropylmethylcellulose is from 0.05% w/v to 1% w/v. The average molecular weight of the hydroxypropylmethylcellulose is from 20 kD to 120 kD.

The viscosity inducing component is used in an amount effective to increase the viscosity of the solution, preferably to a viscosity in the range of about 1.5 to about 30, or even as high as about 750, cps at 25° C., as determined by USP test method No. 911 (USP 23, 1995).

A chelating or sequestering can be included in an amount effective to enhance the effectiveness of the cationic antimicrobial component and/or to complex with metal ions to provide more effective cleaning of the contact lens. A wide range of organic acids, amines or compounds which include an acid group and an amine function are capable of acting as chelating components. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being one of the preferred chelating components.

Three of the four leading contact lens care solutions sold in the U.S. contain disodium ethylenediamine tetraacetic acid ($Na_2EDTA$), however, $Na_2EDTA$ is not biodegradable. As an alternative, one can substitute the EDTA with disuccinate agents. The use of the disuccinate agents has little or no effect on the biocidal efficacy or the cleaning ability of the solutions.

Accordingly, the ophthalmic compositions can include a disuccinate of formula

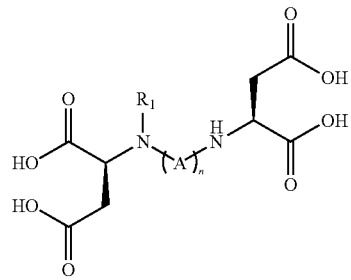

or a corresponding salt thereof; wherein $R_1$ is selected from hydrogen, alkyl or —C(O)alkyl, the alkyl having one to twelve carbons and optionally one or more oxygen atoms, A is a methylene group or an oxyalkylene group, and n is from 2 to 8.

In one embodiment, the disuccinate present in the composition is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below.

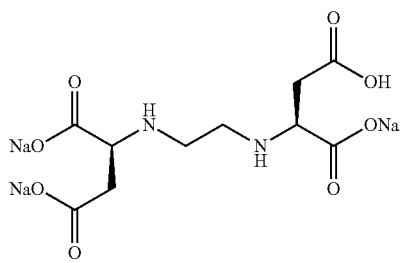

Trisodium salt of EDDS

Typically, the disuccinate is added with the other aqueous components of an ophthalmic composition as its corresponding salt. The salts can include the alkali metals of Group IA such as sodium and potassium. The salts can also include the alkaline earth metals such as calcium or magnesium. The zinc or silver salt of the disuccinate can also be used in the ophthalmic compositions.

Yet another suitable ophthalmic composition component comprises one or more tonicity agents. Tonicity agents (also called osmolality-adjusting agents) serve to have the compositions herein approximate the osmotic pressure of normal lachrymal fluids, which is equivalent to a 0.9 percent solution of sodium chloride or 2.5 percent glycerin solution. Examples of suitable tonicity agents include but are not limited to sodium and potassium chloride; monosaccharides such as dextrose, mannose, sorbitol and mannitol; low molecular weight polyols such as glycerin and propylene glycol; and calcium and magnesium chloride.

These tonicity agents are typically used individually in the ophthalmic compositions herein in amounts ranging from about 0.01 wt % to about 2.5 percent wt %. The tonicity agents allow the formulator to adjust the osmolality of the compositions in a range from 200 mOsmol/kg to 420 mOsmol/kg, or typically from 240 mOsmol/kg to 320 mOsmol/kg.

Accordingly, the compositions of the invention can be used in an aqueous solution to disinfect contact lenses. In general, such a method would include contacting or soaking the lenses with the solution for a period of time, typically for a minimum of one to four hours. Although such contacting may be accomplished by simply soaking a lens in the ophthalmic composition, greater preserving, disinfecting and/or cleaning may possibly be achieved if a few drops of the solution are initially placed on each side of the lens, and the lens is rubbed for a period of time, for example, approximately 20 seconds. The lens can then be subsequently immersed within several milliliters of the solution. Preferably, the lens is permitted to soak in the solution for at least four hours. Furthermore, the lens is preferably rinsed with fresh composition after any rubbing step and again after being immersed within the solution. The lenses are removed from the solution, rinsed with the same or a different solution, for example, a preserved isotonic saline solution, and repositioned on the eye.

The formulated contact lens solutions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The ophthalmic compositions of the invention can also be formulated for use as a preservative solution or packaging solution for contact lenses. One of ordinary skill in the art would know how to adjust the formulation for each of these respective applications.

The ophthalmic compositions can be used as a preservative in ophthalmic formulations for treating patients with dry eye. In such a method, the ophthalmic formulation is administered to the patient's eye, eye lid or to the skin surrounding the patient's eye. The formulation can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

Alternatively, the ophthalmic compositions can be used in ophthalmic formulations for treating an ocular disease or ocular condition. In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

EXAMPLES

Example 1

Stand Alone Disinfectant Test

This example illustrates the effect of the borate/diglycine buffer combination on the antimicrobial efficacy of alexidine dihydrochloride in comparison to that of the individual buffers alone and to carbonate buffer. The antimicrobiocidal efficacy of alexidine dihydrochloride in different buffer systems has been evaluated based upon the performance requirement referred to as the "Stand-Alone Procedure for Disinfecting Products" as outlined by the U.S. Food and Drug Administration, Division of Ophthalmic Devices.[1] The formulations tested are in Table 1. The microorganisms challenged in this procedure include: *Pseudomonas aeruginosa* (ATCC 9027), *Staphylococcus aureus* (ATCC 6538), *Serratia marcescens* (ATCC 13880), *Candida albicans* (ATCC 10231) and *Fusarium solani* (ATCC 36031). The log reduction of microorganisms produced by each formulation is shown in Table 2.

TABLE 1

Alexidine 2HCl with borate/diglycine.

| Component (% w/w) | Comp. Ex. 1 | Comp Ex. 2 | Comp. Ex. 3 | Ex. 1 |
|---|---|---|---|---|
| boric acid | 0.223 | — | — | 0.223 |
| sodium borate | 0.077 | — | — | 0.077 |
| diglycine | — | 0.50 | — | 0.50 |
| sodium carbonate | — | — | 0.25 | — |
| glycerin | 1.0 | 1.0 | 1.0 | 1.0 |
| alexidine 2HCl (ppm) | 1 | 1 | 1 | 1 |
| pH | 7.23 | 7.21* | 7.32* | 7.20 |
| osmolality | 286 | 291 | 294 | 283 |

*pH adjusted with NaOH or HCl

TABLE 2

Biocidal Efficacy of Alexidine HCl in Buffer Solutions

| Example | Time (hr) | Sa | Pa | Sm | Ca | Fs |
|---|---|---|---|---|---|---|
| Comp. 1 | 1 | 3.7 | 2.7 | 2.7 | 1.9 | 2.1 |
|  | 4 | 4.3 | 4.5 | 3.2 | 2.2 | 4.0 |
| Comp. 2 | 1 | 4.8 | 4.4 | 3.0 | 1.9 | 2.1 |
|  | 4 | >4.8 | >4.7 | 3.7 | 2.0 | 3.3 |
| Comp. 3 | 1 | 1.5 | 2.1 | 1.3 | 0.6 | TNTC |
|  | 4 | 2.6 | 3.4 | 2.6 | 0.8 | 2.0 |
| Ex. 1 | 1 | >4.8 | 4.0 | 2.9 | 2.3 | 2.3 |
|  | 4 | >4.8 | >4.7 | 4.1 | 3.1 | 3.2 |

*testing done in the presence of 10% organic soil.
TNTC - too numerous to count
Sa - *S. aureus*
Pa - *P. Aeruginosa*
Sm - *S. Marcescens*
Ca - *C. Albicans*
Fs - *F. Solani*

The stand-alone biocidal results suggest that the combined diglycine/borate buffer enhances the efficacy of alexidine dihydrochloride against *S. marcescens* and *C. albicans* in comparison to the either buffer alone including borate alone.

Example 2

No Rub/No Rinse Regimen Test

This example focuses on the antimicrobial efficacy of model multi-purpose lens care compositions containing diglycine buffer, borate buffer, and combination of the two. In order to distinguish the differences in the antimicrobial efficacy of the model multi-purpose compositions (Table 3), the prototype formulations were subjected to a passive no rub, no rinse regimen.[2] The regimen test involved adding 10 mL of the test solution to each well of a lens case containing a PureVision lens inoculated with a given microorganism. The case was shaken for 10 consecutive seconds. The lens was then allowed to soak in the test solution for 4 hours. The number of viable colony-forming units of microorganism that survive the regimen are determined. The results of the regimen test are outlined in Table 4.

TABLE 3

Multi-purpose lens care compositions

| Formulation (wt. %) | Comp. Ex. 4 | Comp. Ex. 5 | Ex. 2 |
|---|---|---|---|
| diglycine | — | 0.5 | 0.5 |
| boric acid | 0.223 | — | 0.223 |
| sodium borate | 0.077 | — | 0.077 |
| NaCl | 0.158 | 0.158 | 0.158 |
| EDTA | 0.025 | 0.025 | 0.025 |
| HAP (30%) | 0.10 | 0.10 | 0.10 |
| glycerin | 1.500 | 1.200 | 1.000 |
| Tetronic 1107 | 1.333 | 1.333 | 1.333 |
| Pluronic F127 | 0.667 | 0.667 | 0.667 |
| Polymer JR | 0.020 | 0.020 | 0.020 |
| alexidine.2HCl | 8.5 ppm | 8.5 ppm | 8.5 ppm |
| pH | 7.18 | 7.20 | 7.17 |
| osmolality mOsm/kg | 286 | 290 | 288 |

TABLE 4

Regimen testing
Average Number of Colony Forming Units

| Example | Sa | Pa | Sm | Ca | Fs |
|---|---|---|---|---|---|
| Comp. 4 | TNTC | TNTC | TNTC | TNTC | TNTC |
| Comp. 5 | 0 | 0 | 0 | 0 | 0 |
| 2 | 0 | 0 | 1 | 2 | 0 |

TNTC—to numerous to count; Sample set = 3

The lens care compositions were tested in a passive, lens care regimen, and the results of such tests indicate that the addition of diglycine to a borate buffer had little or no affect. One other advantage of the borate/diglycine buffer is that one need not add sufficient amounts of base to adjust the pH to a desired range.

Example 3

No Rub/No Rinse Regimen Test

This example compares the antimicrobial efficacy of borate, carbonate, and 2-amino-2-methyl-1,3-propanediol (AMPD) in combination with diglycine. The formulations tested are in Table 5.

The compositions were tested in a no rub, no rinse regimen. The regimen involved placing PureVision lenses in a 13 mL volume lens case, filling each well with 10 mL of test solution followed by a 10 second shake of the lens case and a 4 hour soak of the lenses. The average number of colony-forming units of microorganisms retrieved from the lens and solution filter combination are outlined in Table 6. The study was conducted with 3 lens samples.

The use of borate buffer in the lens care composition containing diglycine exhibited improved antimicrobial efficacy against the yeast *C. albicans*, which is traditionally one of the more difficult microorganism to kill. Even in the presence of an additional antimicrobial compound I-terpinen-4-ol, the compositions without borate buffer did not exhibit as great of potency against *C. albicans* as the solution with borate buffer that did not contain the additional antimicrobial agent.

TABLE 5

Diglycine in combination with other buffers

| Example | Comp. 6 | Comp. 7 | 3 |
|---|---|---|---|
| diglycine | 0.5 | 0.5 | 0.5 |
| AMPD | 0.042 | — | — |
| sodium carbonate | — | 0.252 | — |
| boric acid | — | — | 0.223 |
| sodium borate | — | — | 0.077 |
| NaCl | 0.1917 | — | 0.157 |
| EDTA | 0.025 | 0.025 | 0.025 |
| glycerin | 1.50 | 1.20 | 1.20 |
| Tetronic 1107 | 1.33 | 1.33 | 1.33 |
| Pluronic F127 | 0.67 | 0.67 | 0.67 |
| 1-terpinen-4-ol | 0.0002 | 0.0002 | — |
| Polymer JR | 0.02 | 0.02 | 0.02 |
| alexidine.2HCl | 0.00085 | 0.00085 | 0.00085 |

TABLE 6

Regimen efficacy of diglycine in combination with other buffers

| | Average Number of Colony-Forming Units | | | | |
|---|---|---|---|---|---|
| Example | Sa | Pa | Sa | Ca | Fs |
| Comp. 6 | 0 | 0 | 0 | 6 | 0 |
| Comp. 7 | 0 | 0 | 0 | 14 | 0 |
| 3 | 0 | 0 | 0 | 0 | 0 |

TNTC—to numerous to count

Example 4

Lens Care Compositions with HPMC and Various Buffer Systems

The lens care compositions listed in Table 7 were prepared and the biocidal efficacy tested against the typical five organisms in a four hour log reduction in the presence of 10% organic soil. The compositions listed in Table 7 can be described as having the following buffer systems: Comparative Examples 6 and 7, borate/citrate; Comparative Examples 8 and 9, borate; Comparative Examples 10 and 11; borate/phosphate; and Examples 6 and 7, borate/diglycine. The biocidal efficacies are reported in Tables 8A and 8B, in which the data of Table 8A is reported at time=0 and the data of Table 8B is the four hour log reduction.

TABLE 7A

| Example | Comp. 8 | Comp. 9 | 4 | 5 |
|---|---|---|---|---|
| sodium citrate | 0.26 | 0.26 | — | — |
| sodium chloride | 0.39 | 0.39 | 0.31 | 0.31 |
| sodium borate | 0.15 | 0.15 | 0.34 | 0.34 |

TABLE 7A-continued

| Example | Comp. 8 | Comp. 9 | 4 | 5 |
|---|---|---|---|---|
| boric acid | 0.45 | 0.45 | 0.45 | 0.45 |
| diglycine | — | — | 0.26 | 0.26 |
| HPMC E15LV | 0.15 | 0.15 | 0.15 | 0.15 |
| tyloxapol | 0.05 | 0.05 | 0.05 | 0.05 |
| Dequest (30% HAP) | 0.10 | 0.10 | 0.05 | 0.05 |
| Na$_2$EDTA | 0.11 | 0.11 | 0.11 | 0.11 |
| polyquaternium-1 (ppm) | 10 | 10 | 10 | 10 |
| PHMB (ppm) | 0.8 | — | 0.8 | — |

TABLE 7B

| Example | Comp. 10 | Comp. 11 | Comp. 12 | Comp. 13 |
|---|---|---|---|---|
| sodium chloride | 0.45 | 0.45 | 0.13 | 0.13 |
| sodium borate | 0.20 | 0.20 | 0.18 | 0.18 |
| boric acid | 0.45 | 0.45 | 0.45 | 0.45 |
| Na phosphate dibasic | — | — | 0.29 | 0.29 |
| Na phosphate monobasic | — | — | 0.02 | 0.02 |
| propylene glycol | — | — | 0.29 | 0.29 |
| Dequest (30% HAP) | 0.10 | 0.10 | 0.10 | 0.10 |
| HPMC E15LV | 0.15 | 0.15 | 0.15 | 0.15 |
| tyloxapol | 0.05 | 0.05 | 0.05 | 0.05 |
| Na$_2$EDTA | 0.11 | 0.11 | 0.11 | 0.11 |
| polyquaternium-1 (ppm) | 10 | 10 | 10 | 10 |
| PHMB (ppm) | 0.8 | — | 0.8 | — |

TABLE 8A

| Example | Sa | Pa | Sm | Ca | Fs | Regimen Test[1] |
|---|---|---|---|---|---|---|
| Comp. 8 | >4.8 | >4.6 | >4.6 | 2.2 | 3.5 | 124, 108, 147 |
| Comp. 9 | 3.7 | >4.6 | 4.9 | 0.9 | 2.0 | 124, 62, 88 |
| Comp. 10 | >4.8 | >4.6 | >4.6 | >4.8 | >4.3 | 0, 0, 0 |
| Comp. 11 | 4.0 | >4.6 | >4.6 | 3.4 | 3.2 | 0, 0, 0 |
| Comp. 12 | >4.8 | >4.6 | >4.6 | >4.8 | 4.3 | 0, 0, 0 |
| Comp. 13 | 4.4 | >4.6 | >4.6 | 3.8 | 3.2 | 0, 0, 0 |
| 4 | >4.8 | >4.6 | >4.6 | >4.8 | >4.3 | 0, 0, 0 |
| 5 | 4.0 | >4.6 | >4.6 | 4.5 | 3.5 | 0, 0, 0 |
| Opti-Free Replenish ® | 3.6 | >4.6 | 3.3 | 2.2 | 3.9 | 155, 135, 191 |

Opti-Free Replenish ® is a commercial lens care solution available from Alcon Laboratories, Inc.
[1]Regimen test conducted with O$_2$Optix contact lens contaminated with *C. albicans* for a five second rinse and six hour soak.

We claim:
1. An ophthalmic composition comprising:
   0.05% w/v to 2% w/v diglycine or a salt thereof;
   1.0 ppm to 8.5 ppm alexidine; and
   0.1% w/v to 2% w/v of one or more boron buffering compounds.
2. The composition of claim 1 further comprising hyaluronic acid or a salt thereof.
3. The ophthalmic composition of claim 1 further comprising a sulphobetaine surfactant of the formula

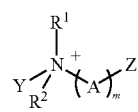

wherein R$^1$ and R$^2$ are independently selected from a C$_1$-C$_4$ alkyl;
A is an unsubstituted or a substituted alkylene with two to four carbons, and m is an integer from 2 to 4;
Y is a straight or branched alkyl, or a straight or branched alkene, with eight to sixteen carbons; and
Z is —SO$_3^-$ or —CO$_2^-$, preferably Z is —SO$_3^-$.

4. The composition of claim 1 further comprising dexpanthenol, sorbitol, propylene glycol, aspartic acid, glycolic acid, 2-amino-2-methyl-1,3-propanediol or any mixture thereof.

5. The composition of claim 1 further comprising hydroxypropylmethyl cellulose.

6. The composition of claim 1 further comprising a disuccinate of formula

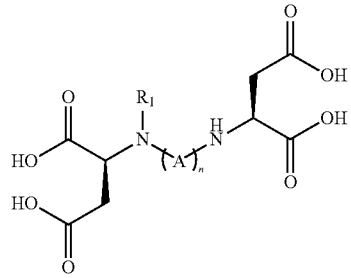

or a corresponding salt thereof; wherein $R_1$ is selected from hydrogen, alkyl or —C(O)alkyl, the alkyl having one to twelve carbons and optionally having one or more oxygen atoms; and A is a methylene group or an oxyalkylene group, and n is from 2 to 10.

7. The composition of claim 1 wherein the one or more boron buffering compounds include boric acid from 0.15% w/v to 0.6% w/v, sodium or potassium borate from 0.05% w/v to 0.5% w/v, and the diglycine from 0.1% w/v to 0.7% w/v.

8. An ophthalmic composition comprising:

buffering compounds including boric acid from 0.15% w/v to 0.6% w/v, sodium or potassium borate from 0.05% w/v to 0.5% w/v, and diglycine from 0.1% w/v to 0.7% w/v;

1.0 ppm to 8.5 ppm alexidine; and hyaluronic acid or a salt thereof, which is present from 0.05 wt. % to 0.2 wt. %.

9. The composition of claim 8 further comprising 1 ppm to 10 ppm of α-[4-tris(2-hydroxyethyl)ammonium chloride-2-butenyl]poly[1-dimethylammonium chloride-2-butenyl]-ω-tris(2-hydroxyethyl) ammonium chloride.

10. The composition of claim 8 further comprising a disuccinate of formula

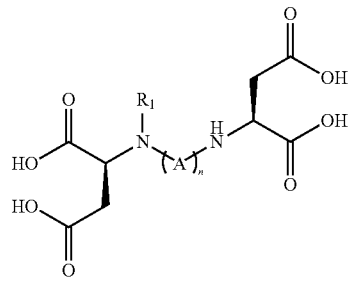

or a corresponding salt thereof; wherein $R_1$ is selected from hydrogen, alkyl or —C(O)alkyl, the alkyl having one to twelve carbons and optionally having one or more oxygen atoms; and A is a methylene group or an oxyalkylene group, and n is from 2 to 10.

11. A method to disinfect contact lenses comprising contacting or soaking the contact lenses with an aqueous ophthalmic composition for a minimum of one to four hours, and repositioning the lenses on the eye, wherein the composition comprises:

0.05% w/v to 2% w/v diglycine or a salt thereof;

1.0 ppm to 8.5 ppm alexidine; and 0.1% w/v to 2% w/v of one or more boron buffering compounds.

12. The method of claim 11 wherein the composition further comprises 1 ppm to 10 ppm α-[4-tris(2-hydroxyethyl) ammonium chloride-2-butenyl]poly[1-dimethylammonium chloride-2-butenyl]-ω-tris(2-hydroxyethyl) ammonium chloride.

\* \* \* \* \*